(12) United States Patent
Kobilka et al.

(10) Patent No.: US 8,076,103 B2
(45) Date of Patent: Dec. 13, 2011

(54) EUKARYOTIC EXPRESSION SYSTEM FOR THE INCORPORATION OF STABLE ISOTOPES INTO PROTEINS

(75) Inventors: Brian Kobilka, Palo Alto, CA (US); Michael Bokoch, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 659 days.

(21) Appl. No.: 12/338,816

(22) Filed: Dec. 18, 2008

(65) Prior Publication Data
US 2009/0171073 A1 Jul. 2, 2009

Related U.S. Application Data

(60) Provisional application No. 61/015,122, filed on Dec. 19, 2007.

(51) Int. Cl.
*C12P 21/06* (2006.01)
*C12N 5/00* (2006.01)
*C12N 15/00* (2006.01)

(52) U.S. Cl. ............... 435/69.1; 435/325; 435/320.1

(58) Field of Classification Search .......... None
See application file for complete search history.

(56) References Cited

U.S. PATENT DOCUMENTS

2006/0035382 A1 2/2006 Shinozaki et al.
2007/0082399 A1 4/2007 Egorova-Zachernyuk

OTHER PUBLICATIONS

Fernandez, et al., Cost-effective production of 13C, 15N stable isotope-labelled biomass from phototrophic microalgae for various biotechnological applications, Biomolecular Engineering, vol. 22, Issues 5-6, Dec. 2005, pp. 193-200.
Gershenzon, et al., The function of terpene natural products in the natural world, Nat Chem Biol. Jul. 2007;3 (7):408-414.
Hale, et al., Expressing and purifying membrane transport proteins in high yield, J Biochem Biophys Methods. Jan. 4, 2002;50(2-3):233-243.
Joost, et al., Phylogenetic analysis of 277 human G-protein-coupled receptors as a tool for the prediction of orphan receptor ligands, Genome Biol. Oct. 17, 2002;3(11):RESEARCH0063. Epub Oct. 17, 2002.
Nassar, et al.,The insecticidal activity of Cyanobacteria against four insects, two of medical importance and two agricultural pests with reference to the action on albino mice, J Egypt Soc Parasitol. 1999;29(3):939-949.
Spencer, et al., Sodium alginate as a gelling agent in diets for the cabbage looper, *Trichoplusia ni*, Entomologia Experimentalis et Applicata, vol. 20, No. 1 / Jan. 1976, North-Holland Publ. Co. Amsterdam.

*Primary Examiner* — Alexander Kim
(74) *Attorney, Agent, or Firm* — Carol L. Francis; Michael B. Rubin; Bozicevic, Field & Francis LLP

(57) ABSTRACT

Methods for producing stable isotope-labeled recombinant protein are provided. The methods include isolating a stable isotope-labeled recombinant protein from a *Trichoplusia ni* larva expressing a recombinant protein, which *Trichoplusia ni* larva has ingested a food source comprising stable isotope-labeled algae, thereby resulting in incorporation of a stable isotope into the recombinant protein to produce the stable isotope-labeled recombinant protein.

13 Claims, 9 Drawing Sheets

Figure 1

| Day | Stage | Max. weight | | |
|---|---|---|---|---|
| -2 | egg | | | Hatch |
| 0 | 1st instar | < 1 mg | | Grow |
| 3 | 2nd instar | 2 mg | control diet | |
| 8 | 3rd instar | 20 mg | | Label |
| 11 | 4th instar | 80 mg | Isotope labeled algae diet | |
| 14 | 5th instar | 120 mg | inject baculovirus  -or-  feed occluded baculovirus | Infect |
| 17 | infected | 200 mg | | Express |

↳ Isolate Protein

Outline of *Trichoplusia ni* larval development, isotope labeling, infection, expression and isolation.

Saturation binding of βAR antagonist [$^3$H]-dihydroalprenolol to T. ni membranes (4 days after oral infection, $K_d$ =1.6 nM, $B_{max}$=16 pmol/mg total protein).

Total $\beta_2$AR expression per larva as estimated by western blot densitometry (anti-FLAG). $\beta_2$AR purified from Sf9 cells was loaded in known amounts to generate a standard curve. In lanes A and B, 1/160th of the total protein from each larva was loaded and quantified.

Removal of larval gut prevents β2AR(RockII) proteolysis (anti-FLAG blot). Larvae were (*B*) dissected to remove the gut or (*C*) not dissected (gut is ruptured during homogenization). (*A*) Wild-type β2AR purified from Sf9 insect cells for comparison.

Larvae expressing β$_2$AR(RockII) were dissected and homogenized in solubilization buffer with protease inhibitors (Lanes *B1* and *B2*) or without protease inhibitors (Lanes *C1* and *C2*), and incubated for 24 hours at 4°C prior to SDS-PAGE. Lane (*A*) Purified wild-type β$_2$AR for comparison.

Figure 9

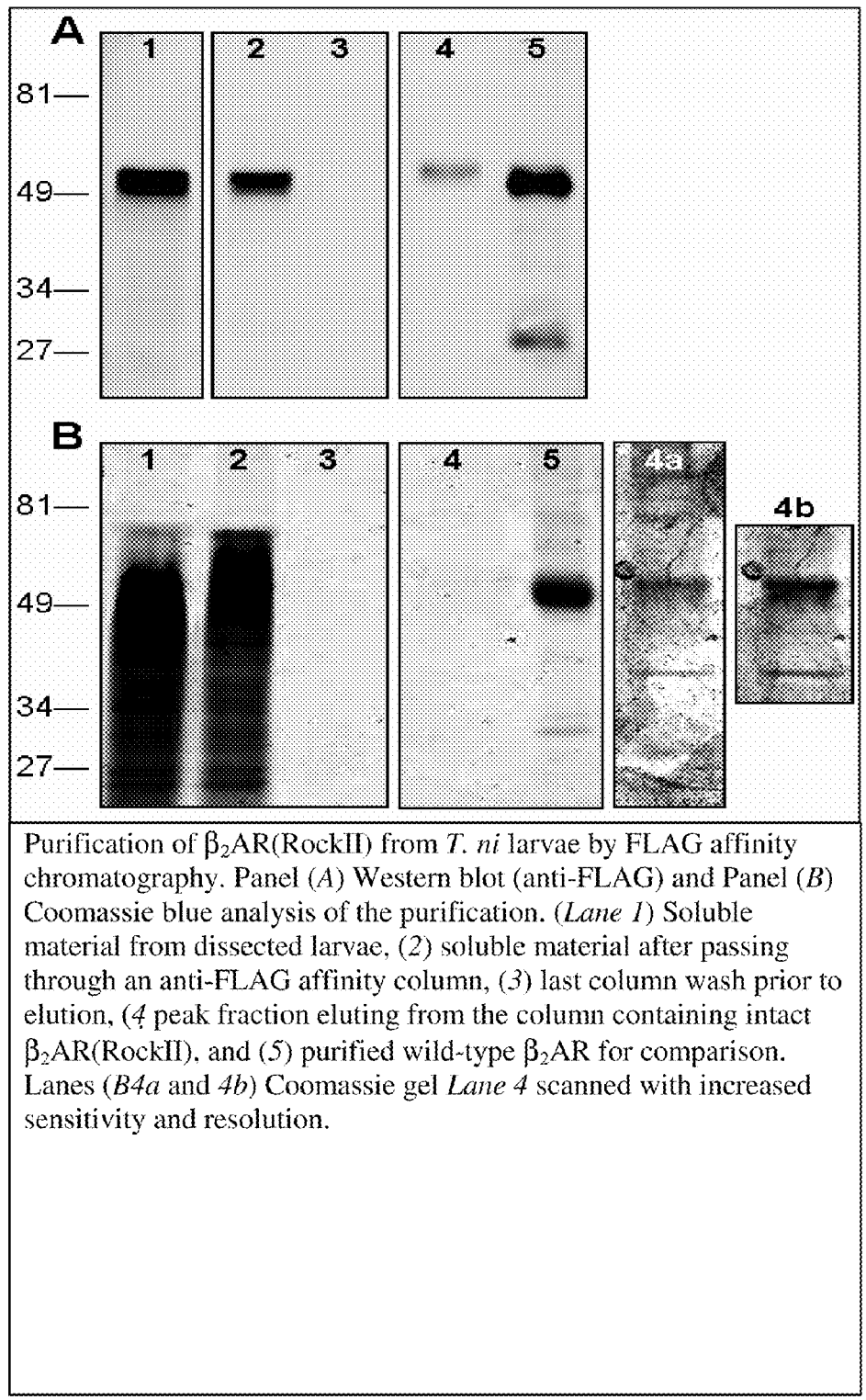

Purification of β₂AR(RockII) from *T. ni* larvae by FLAG affinity chromatography. Panel (*A*) Western blot (anti-FLAG) and Panel (*B*) Coomassie blue analysis of the purification. (*Lane 1*) Soluble material from dissected larvae, (*2*) soluble material after passing through an anti-FLAG affinity column, (*3*) last column wash prior to elution, (*4*) peak fraction eluting from the column containing intact β₂AR(RockII), and (*5*) purified wild-type β₂AR for comparison. Lanes (*B4a* and *4b*) Coomassie gel *Lane 4* scanned with increased sensitivity and resolution.

EUKARYOTIC EXPRESSION SYSTEM FOR THE INCORPORATION OF STABLE ISOTOPES INTO PROTEINS

CROSS REFERENCE TO RELATED APPLICATIONS

This application claims priority to U.S. Provisional Patent Application No. 61/015,122, filed Dec. 19, 2007, which is incorporated herein by reference in its entirety and for all purposes.

STATEMENT REGARDING FEDERALLY SPONSORED RESEARCH

The U.S. government has certain rights in this invention, pursuant to Grant No. RO1 NS28471 awarded by the National Institutes of Health.

BACKGROUND

Nuclear Magnetic Resonance (NMR) Spectroscopy involves placing a molecule to be analyzed in a powerful magnetic field and irradiating it with a strong radio signal. The nuclei of the various atoms will align themselves with the magnetic field until energized by the radio signal. They then absorb this energy and re-radiate (resonate) it at a frequency dependent on the type of nucleus and the chemical environment as largely determined by bonding of the nucleus. Moreover, resonances can be transmitted from one nucleus to another, either through bonds or through 3-D space, thus giving information about the environment of a particular nucleus and nuclei in its vicinity.

Not all isotopes of the same element are NMR active. For larger molecules, such as proteins, a sufficiently strong signal in NMR spectra requires enrichment with NMR active stable isotopes. The most commonly used stable isotopes for macromolecular NMR are $^{13}C$ and $^{15}N$.

NMR has been successfully applied to determine the structures of over 2,500 proteins. The list of successful structures is dominated by relatively small (<40 kDa) soluble proteins that can be readily expressed in bacteria, which are capable of producing large amounts of soluble proteins uniformly labeled with the stable isotopes $^{13}C$ and $^{15}N$. However, not all proteins are amenable to production and purification using bacterial expression systems. This is particularly true for mammalian membrane proteins which may undergo significant post-translational modifications including appropriate folding, cross-linking of inter- and intra-molecular chains through disulphide bridges, glycosylation, acylation, phosphorylation and other chemical modifications.

The limited success of *E. coli* for mammalian membrane protein expression is a major barrier to NMR experiments because *E. coli* are currently the most economical system for producing $^{13}C$ and $^{15}N$ labeled proteins. Bacterial media for stable isotope labeling is relatively inexpensive. *E. coli* can grow on $^{13}C$-glucose or ($^{13}C$-glycerol) as the sole carbon source, and $^{15}NH_4Cl$ or $^{15}(NH_4)_2SO_4$ as a nitrogen source. The estimated cost of $^{13}C/^{15}N$ bacterial media is about $1,500 to $3,000 per liter (Studier, F. W. 2005 *Protein Expr. Purif.* 41(1):207-234). *Pichia Pastoris* is a methylotrophic yeast currently used as an alternative to bacteria for isotope labeling. *P. Pastoris* can ferment $^{13}C$-methanol as the major carbon source, supplemented with $^{13}C$-glycerol during a brief initial batch phase (again, inexpensive $^{15}NH_4^+$ salts serve as the sole nitrogen source). Although the basic ingredients are similar, the nature of large-scale fermentation requires constant infusion of different components over several days. As such, the cost of uniform $^{13}C/^{15}N$ isotope labeling rises to an estimated $36,800 per liter of fermentation (Van den burg et al. 2001 *J. Biomol. NMR* 20(3):251-261). Expression in higher eukaryotic cells grown in culture (insect and mammalian) is also relatively expensive, given that no simple carbon/nitrogen source can be used. Isotope-labeled amino acids must be supplemented one-by-one into the complex media, resulting in costs of approximately $23,000 per liter for labeled insect cells.

Thus, there is a need in the art for additional methods for the economical incorporation of stable isotopes into proteins for NMR studies, particularly with regard to mammalian membrane proteins of interest such as G-Protein Coupled Receptors (GPCRs).

LITERATURE

Fernandez et al. (2005) *Biomolecular Engineering* 22:193-200; Hale et al. (2002) *J. Biochem. Biophys. Methods* 50:233-243; Spencer et al. (1975) *Ent. Exp. & Appl.* 20:39-42; Nassar et al. (1999) *J. Egypt. Soc. Parasitology* 29(3):939-949; U.S. Patent Application Publication No. 2007/0082399; and U.S. Patent Application Publication No. 2006/0035382.

SUMMARY OF THE INVENTION

Methods for producing stable isotope-labeled recombinant protein are provided. The methods include isolating a stable isotope-labeled recombinant protein from a *Trichoplusia ni* larva expressing a recombinant protein, which *Trichoplusia ni* larva has ingested a food source comprising stable isotope-labeled algae, thereby resulting in incorporation of a stable isotope into the recombinant protein to produce the stable isotope-labeled recombinant protein.

A variety of stable isotopes may be utilized in connection with the disclosed methods. For example, in one aspect of the disclosed methods, the stable isotope is selected from the group consisting of $^{13}C$, $^{15}N$, $^2H$, and combinations thereof.

Stable isotope-labeled algae may be produced by growing algae in the presence of an isotope-labeled carbon, nitrogen or hydrogen source. For example, the stable isotope-labeled algae may be produced by growing algae in the presence of at least one of $^{15}NH_3$, $^{15}NO_3^-$, $^{15}NO_2^-$, $H^{13}CO_3^-$, $^{15}N_2$, $^{13}CO_2$, $Na^{15}NO_3$ and $^2H_2O$.

In one aspect of the disclosed methods, the stable isotope-labeled algae are labeled with $^{13}C$. For example, at least 90% of the carbon atoms in the stable isotope-labeled algae are $^{13}C$. In another aspect of the disclosed methods, where the stable isotope-labeled algae are labeled with $^{13}C$, at least 60% of the carbon atoms in the stable isotope-labeled recombinant protein are $^{13}C$.

In one aspect of the disclosed methods, the stable isotope-labeled algae are labeled with $^{15}N$. For example, at least 90% of the nitrogen atoms in the stable isotope-labeled algae are $^{15}N$. In another aspect of the disclosed methods, where the stable isotope-labeled algae are labeled with $^{15}N$, at least 60% of the nitrogen atoms in the stable isotope-labeled recombinant protein are $^{15}N$.

In certain aspects of the disclosed methods, the stable isotope-labeled algae are labeled with both $^{13}C$ and $^{15}N$. For example, at least 90% of the carbon atoms in the stable isotope-labeled algae are $^{13}C$ and at least 90% of the nitrogen atoms in the stable isotope-labeled algae are $^{15}N$. In one aspect of the disclosed methods, where the stable isotope-labeled algae are labeled with both $^{13}C$ and $^{15}N$, at least 60% of the carbon atoms in the stable isotope-labeled recombinant protein are $^{13}$C and at least 60% of nitrogen atoms in the stable isotope-labeled recombinant protein are $^{15}$N.

Expression of the recombinant protein in the *Trichoplusia ni* larva may be accomplished by a variety of methods known in the art. For example, the *Trichoplusia ni* larva may be infected with a baculovirus comprising a nucleic acid encoding the recombinant protein.

The disclosed methods find use in a variety of applications where isotope-labeled proteins are utilized, e.g., NMR analysis.

BRIEF DESCRIPTION OF THE DRAWINGS

FIG. 1 shows a schematic of *Trichoplusia ni* larval development, isotope labeling, infection, expression, and isolation.

FIG. 9 shows the results (Western Blot-Panel A and Coomassie Blue-Panel B) of the purification of β$_2$AR (RockII) from *T. ni* larvae by FLAG affinity chromatography. (Lane 1) Soluble material from dissected larvae, (2) soluble material after passing through an anti-FLAG affinity column, (3) last column wash prior to elution, (4 peak fraction eluting from the column containing intact β$_2$AR (RockII), and (5) purified wild-type β$_2$AR for comparison. Lanes (B4a and 4b) Coomassie gel Lane 4 scanned with increased sensitivity and resolution.

Figure 2:
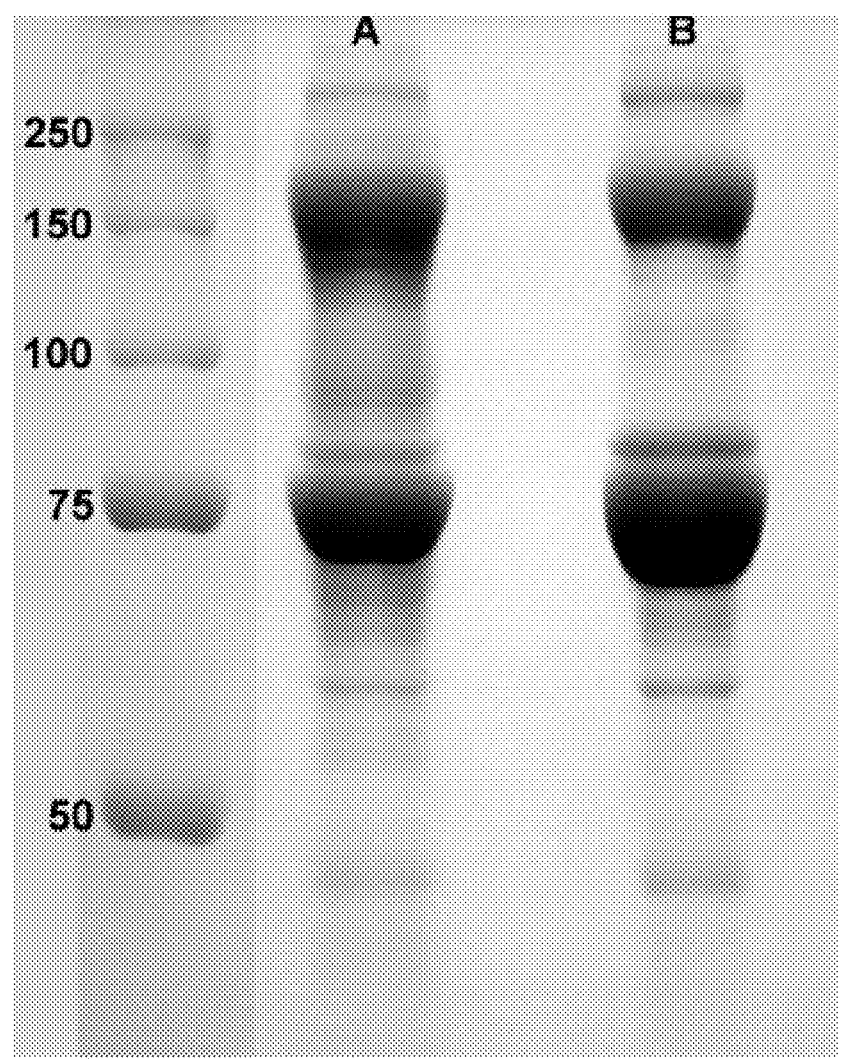
FIG. 2 shows the results of a Coomassie stain of SDS-PAGE of hemolymph from *Trichoplusia ni* raised on (A) control diet or (B) $^{13}$C blue-green algae diet.

Before the present invention is further described, it is to be understood that this invention is not limited to the particular embodiments described, as such embodiments may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

DEFINITIONS

It must be noted that as used herein and in the appended claims, the singular forms "a," "an," "and," and "the" include plural referents unless the context clearly dictates otherwise. Thus, for example, reference to "a stable isotope" includes a plurality of such stable isotopes and reference to "the recombinant protein" includes reference to one or more recombinant proteins and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein the terms "alga," "algae," and "algal" refer to a prokaryotic or eukaryotic organism(s) belonging to one of the following phyla: Cyanophyta-(Cyanobacteria, bacteria/blue-green algae), Rhodophyta (red algae), Euglenophyta (euglenoids), Cryptophyta (cryptomonads), Pyrrophyta (dinoflagellates), Raphidophyta, Haptophyta (Prymnesiophyta), Chrysophyta (golden/golden brown algae), Xanthophyta (Tribophyta; yellow-green algae), Chlorophyta (green algae, include stoneworts), Eustigmatophyta, Phaeophyta (Fucophyta, brown algae), Prasinophyta, Bacillariophyta (diatoms), and Glaucophyta. The above terms are also meant to encompass genetically modified versions of the above organisms.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, cDNA, recombinant polynucleotides, plasmids, vectors, isolated DNA of any sequence, control regions, isolated RNA of any sequence, nucleic acid probes, and primers. The nucleic acid molecule may be linear or circular.

The term "isolated" refers to separation of an entity (e.g., polypeptide, nucleic acid, etc.) from other entities with which they are naturally associated or may be associated during synthesis (e.g., recombinant, chemical synthesis, etc.). The term "isolated" means an entity is not in a state in which it is found in nature or, where the entity is produced by recombinant or other synthetic means, is separated or enriched relative to other components that may be present. Thus, for example, an "isolated protein" is not as it appears in nature but may be substantially less than 100% pure protein. For example, an isolated entity (e.g., a polypeptide) may make up greater than about 50% of the total content of the composition (e.g., total protein of the composition) and typically, greater than about 60% of the total protein content. More typically, an isolated protein will be one which makes up at least 75%, at least 80%, at least 85%, at least 90%, at least 95%, or more of the total content of the composition (e.g., total protein of the composition).

A "coding sequence", or a sequence that "encodes" a selected polypeptide, is a nucleic acid molecule which is transcribed (in the case of DNA) and translated (in the case of mRNA) into a polypeptide, for example, in-vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Encoded by" refers to a nucleic acid sequence which codes for a gene product, such as a polypeptide. Where the gene product is a polypeptide, the polypeptide sequence or a portion thereof contains an amino acid sequence of at least 3 to 5 amino acids, typically at least 8 to 10 amino acids, and even more typically at least 15 to 20 amino acids from a polypeptide encoded by the nucleic acid sequence.

"Operably linked" refers to an arrangement of elements wherein the components so described are configured so as to perform their usual function. In the case of a promoter, a promoter that is operably linked to a coding sequence will effect the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

A "vector" is capable of transferring gene sequences to target cells. Typically, the terms "expression vector," and "gene transfer vector," mean any nucleic acid construct capable of directing the expression of a gene of interest in a host cell. Thus, the term includes cloning, and expression vehicles, as well as integrating vectors.

An "expression cassette" comprises any nucleic acid construct capable of directing the expression of a gene/coding sequence of interest, which is operably linked to a promoter of the expression cassette. Such cassettes can be constructed into a "vector," "expression vector," or "gene transfer vector," in order to transfer the expression cassette into target cells. Thus, the term includes cloning and expression vehicles, as well as viral vectors.

The term "recombinant," as used in connection with a DNA molecule, means that a particular DNA sequence is the product of various combinations of cloning, restriction, and/or ligation steps resulting in a construct having a structural coding sequence distinguishable from homologous sequences found in natural systems. Generally, DNA sequences encoding the structural coding sequence can be assembled from cDNA fragments and short oligonucleotide linkers, or from a series of oligonucleotides, to provide a synthetic gene which is capable of being expressed in a recombinant transcriptional unit. Such sequences can be provided in the form of an open reading frame uninterrupted by internal nontranslated sequences, or introns, which are typically present in eukaryotic genes. Genomic DNA comprising the relevant sequences could also be used. Sequences of non-translated DNA may be present 5' or 3' from the open reading frame, where such sequences do not interfere with manipulation or expression of the coding regions. Thus, e.g., the term "recombinant" polynucleotide or nucleic acid refers to one which is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

Similarly, a "recombinant polypeptide" or "recombinant protein" refers to a polypeptide or protein which is not naturally occurring, or is made by the artificial combination of two otherwise separated segments of amino acid sequences. This artificial combination may be accomplished by standard techniques of recombinant DNA technology, such as described above, i.e., a recombinant polypeptide or recombinant protein may be encoded by a recombinant polynucleotide. Thus, a recombinant polypeptide or recombinant protein is an amino acid sequence encoded by all or a portion of a recombinant polynucleotide. The definition includes, but is not limited to, the production of a protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below. Conformationally restrained polypeptides such as cyclic peptides are also encompassed by the term "polypeptide".

The term "fusion protein" and grammatical equivalents thereof means a protein composed of a plurality of polypeptide components, that while typically unjoined in their native state, typically are joined by their respective amino and carboxyl termini through a peptide linkage to form a single continuous polypeptide. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an immunological tag, a detectable fusion partner, such as a fluorescent protein, β-galactosidase, luciferase, etc., and the like.

The term "endogenous", when used in reference to a biopolymer, means a biopolymer which is naturally produced (e.g., by an unmodified mammalian or human cell). As used herein, the terms "endogenous" and "native" are interchangeable.

A "deletion" is defined as a change in the sequence of a biopolymer in which one or more residues are absent as compared to a sequence of a parental biopolymer. For example, a deletion can remove about 2, about 5, about 10, up to about 20, up to about 30 or up to about 50 or more amino acids. A biopolymer may contain more than one deletion.

An "insertion" or "addition" is a change in a sequence of a biopolymer that results in the addition of one or more residues, as compared to a sequence of a parental biopolymer. "Insertion" generally refers to addition to one or more residues within a biopolymer, while "addition" can be an insertion or refer to amino acid residues added at an end, or both termini, of a biopolymer. For example, an insertion or addition is usually of about 1, about 3, about 5, about 10, up to about 20, up to about 30 or up to about 50 or more amino acids. A biopolymer may contain more than one insertion or addition.

A "substitution" results from the replacement of one or more residues of a biopolymer by different residues, as compared to a sequence of a parental biopolymer. It is understood that a polypeptide may have conservative amino acid substitutions which have substantially no effect on activity of the polypeptide. A conservative amino acid substitution is one in which an amino acid is substituted for another amino acid having similar properties such that the folding or activity of the protein is not significantly affected. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent.

The term "stable isotope" refers to an isotope of a chemical element which is not spontaneously radioactive.

The terms "stable isotope-labeled" and "isotopically labeled" are used interchangeably herein to refer to material, e.g., a protein, algae, etc., which is modified to incorporate one or more stable isotopes, such that the modified material comprises more atoms of a given element in a particular stable isotopic form than occurs in the material naturally. For example, a protein isotopically labeled with $^{13}C$ is a protein which has been modified to incorporate $^{13}C$ to levels greater than those that occur in the protein naturally. Thus, a protein having a 1% natural abundance of $^{13}C$ is considered isotopically labeled when the protein is expressed under conditions which result in the incorporation of $^{13}C$ into the protein to levels greater than 1%.

As used herein, an indication that a molecule or material, e.g., a protein, is "detectably labeled" means that the molecule or material has been modified to incorporate a sufficient amount of the desired stable isotope, such that the molecule or material is detectable, using, for example, techniques such as NMR spectroscopy. In the case of NMR-active isotopes, such as $^{13}C$ and $^{15}N$, a detectably labeled molecule or material is generally modified to incorporate a sufficient amount of $^{13}C$ and/or $^{15}N$ such that NMR spectra can be generated using the molecule or material, e.g., to facilitate analysis three-dimensional structure of a labeled protein. In general, in the context of the present invention, this means that at least 60% of the atoms of a given element will be in the desired stable isotopic form, usually at least 65%, 70%, 75%, 80%, 85%, 90%, 95% or 99.9%.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Methods for isolating a stable isotope-labeled recombinant protein are provided. The methods comprise isolating a stable isotope-labeled recombinant protein from a *Trichoplusia ni* larva expressing a recombinant protein, which *Trichoplusia ni* larva has ingested a food source comprising stable isotope-labeled algae, thereby resulting in incorporation of a stable isotope into the recombinant protein to produce the stable isotope-labeled recombinant protein.

Algae Suitable for Use in the Disclosed Methods

A variety of algal organisms find use in the disclosed methods. Suitable organisms include those organisms belonging to one of the following phyla: Cyanophyta (Cyanobacteria/blue-green algae), Rhodophyta (red algae), Euglenophyta (euglenoids), Cryptophyta (cryptomonads), Pyrrophyta (dinoflagellates), Raphidophyta, Haptophyta (Prymnesiophyta), Chrysophyta (golden/golden brown algae), Xanthophyta (Tribophyta; yellow-green algae), Chlorophyta (green algae, include stoneworts), Eustigmatophyta, Phaeophyta (Fucophyta, brown algae), Prasinophyta, Bacillariophyta (diatoms), and Glaucophyta.

The following examples are given of suitable genera within these phyla which may be used in the methods disclosed herein.

Cyanophyta (Cyanobacteria/blue-green algae): *Agmenellum, Spirulina, Synechoccus, Anabaena*, and *Microcystis*.

Chlorophyta (green algae): *Chlorella, Neochloris, Scenedesmus, Dunaliella, Haematococcus,* and *Staurastrum*. Rhodophyta (red algae): *Porphyridium, Cyanidium, Cystoclonium,* and *Audouinella*. Cyanidiophyceae (thermophilic Rhodophyceae): *Cyanidium, Galdiera,* and *Cyanidioschyzon*. Phaeophyta (brown algae): *Ectocarpus* and *Streblonema*. Algae from the group of heterokontophyta (heterokont chromophytes), prymnesiophyta (haptophyta), bacillariophyceae (diatoms), chryptophyta, dinophyta (pyrrhophyta, dinoflagelletes), and euglenophyta (euglenoids). Heterokontophyta: *Rhinomonas, Syncripta,* and *Heteroccus*. Prymnesiophyta (haptophyta): *Pseudoisochrysis, Phaeocystis, Prymnesium,* or *Emiliania*. Chrysophyta group including Bacillariophyta class Bacillariophyceae (diatoms): *Phaeodactylum, Navicula, Nitzchia, Amphora, Centronella, Eucampia, Fragilaria,* Chrysophyta class Chrysophyceae (golden algae), Haptophyta class Haptophyceae. Chryptophyta: *Cryptomonas, Chroomonas,* and *Rhodomonas*. Dinophyta: *Peridinium, Oxyrrhis,* and *Crypthecodinium*. Euglenophyta: *Euglena* and *Astasia*.

Of particular interest are those microscopic species of the above phyla and genera which are phototrophic. These organisms, referred to hereinafter as "microalgae," comprise uni- and oligocellular phototrophic organisms, including eukaryotic green, red, and gold algae, diatoms and dinoflagellates as well as prokaryotic cyanobacteria (blue-green algae).

Of further interest are those species of microalgae which are aquatic, i.e., which occur naturally in either marine or freshwater environments. By way of example, one species of particular interest is the cyanobacteria *Agmenellum quadruplicatum*.

Labeling of Algae with Stable Isotopes

The methods disclosed herein involve the expression of a recombinant protein in a *Trichoplusia ni* larva which has ingested a food source comprising stable isotope-labeled algae. In one aspect of the disclosed methods, stable isotopes of interest are those stable isotopes which when incorporated into a polypeptide of interest render the polypeptide suitable for use in NMR analysis.

Stable isotopes which may be incorporated into algae to produce stable isotope-labeled algae for use in the disclosed methods include stable isotopes commonly used in connection with NMR analysis of proteins, e.g., $^{13}C$, $^{15}N$, $^{2}H$ and combinations thereof.

Thus, in one aspect of the disclosed methods the stable isotope-labeled algae are labeled with $^{13}C$, $^{15}N$ or $^{2}H$. In another aspect, the isotope-labeled algae are labeled with two or more stable isotopes, e.g., C and $^{13}N$, $^{15}C$ and $^{2}H$, or $^{15}N$ and $^{2}H$.

Stable isotopes may be incorporated into algae to produce stable isotope-labeled algae by growing the algae on simple, inexpensive carbon and nitrogen sources, such as $^{15}NH_3$, $^{15}NO_3^-$, $^{15}NO_2^-$, $H^{13}CO_3^-$, $^{15}N_2$, $^{13}CO_2$, $Na^{15}NO_3$ or combinations thereof. $^{2}H_2O$ may also be utilized for the incorporation of H. An exemplary method for the production of $^{13}C/^{15}N$ labeled algae is described in Fernandez et al. 2005 *Biomolecular Engineering* 22: 193-200.

Stable isotope-labeled algal cells are also available in lyophilized form from companies such as Cambridge Isotope Laboratories, Inc., 50 Frontage Road, Andover, Mass. 01810-5413, USA.

The isotope-labeled algae used in the disclosed methods are typically labeled at levels such that stable isotopes of the stable isotope-labeled algae are incorporated into *T. ni* larval proteins following ingestion of the stable isotope-labeled algae by the *T. ni* larvae within a desired period of time. For example, a suitable period of time for the incorporation of stable isotope into *T. ni* larval proteins following ingestion of stable isotope-labeled algae by *T. ni* larvae is from about 8 to about 14 days. Thus, in some embodiments, the isotope labeled algae used in the disclosed methods are labeled at levels such that stable isotopes of the stable isotope-labeled algae are incorporated into *T. ni* larval proteins in about 8 to about 14 days, about 9 to about 13 days, about 10 to about 12 days, about 13 days, about 12 days, about 11 days, about 10 days, about 9 days, or about 8 days, usually about 10 days. In one particular embodiment, this period of time will be at least 10 days. Typically, in the stable isotope-labeled algae, at least 65% of the atoms of a given element are in the desired stable isotopic form, more typically at least 70%, 75%, 80% or 85%, and most typically at least 90%, 95% or 99%. For example, in one embodiment at least 95%, at least 98% or at least 99% of the carbon atoms in the isotope-labeled algae are $^{13}C$. In another embodiment, at least 95%, at least 98% or at least 99% of the nitrogen atoms in the isotope-labeled algae are $^{15}N$. In a further embodiment, at least 95%, at least 98%, or at least 99% of the carbon atoms in the isotope-labeled algae are $^{13}C$, and at least 95%, at least 98% or at least 99% of the nitrogen atoms in the isotope-labeled algae are $^{15}N$.

Growth and Infection of *T. ni* Larvae

The larvae of the cabbage looper (*Trichoplusia ni*) are used in the methods disclosed herein for the expression and isolation of isotope-labeled recombinant proteins of interest. Methods of raising *T. ni* larvae for use in the expression of recombinant proteins are known in the art. See, for example, Medin et al. (1990) *Proc. Natl. Acad. Sci.* 87: 2760-2764, which describes larval growth conditions on pages 2761-2762, which pages are incorporated by reference herein.

During development, *T. ni* larvae pass through five molting stages or "instars", with the 5th instar ending in pupae formation. The larvae grow from a mass of less than one milligram (1st instar) to approximately 150-200 mg (5th instar).

Generally, in connection with the methods disclosed herein, *T. ni* larvae are hatched from eggs, fed a food source comprising isotope-labeled algae, and allowed to grow for approximately 14 days (or until $4^{th}$ or $5^{th}$ instar). Optionally, the larvae are fed a non-labeled food source, such as a traditional insect diet for a period of time, e.g., through $2^{nd}$ instar, and then switched to a food source comprising stable isotope-labeled algae. At approximately $4^{th}$ or $5^{th}$ instar, the larvae are infected with a baculovirus vector which comprises a nucleic acid encoding the recombinant protein of interest. In particular embodiments, larvae are not infected before the $5^{th}$ instar in order to provide larvae of a desired size at harvest. After approximately 3 to 4 days post infection, larvae are harvested and optionally frozen at −70° C. In some embodiments, the infection period ranges from about 3 to about 5 days. For example, the larvae may be harvested at about 3, 4, or 5 days post infection, usually prior to 5 days such that the larvae have not died as a result of the infection. In particular embodiments, the larvae are harvested at about 3, about 3.5, about 4, or about 4.5 days post infection.

In one aspect of the disclosed methods, the larvae are hatched and raised in a climate controlled chamber that is held at approximately 25° C. and 50% relative humidity, with a fixed light:dark (14 hours:10 hours) cycle as described in O'Reilly et al. 1997 *Methods Mol. Biol.* 62:235-246.

An exemplary method suitable for use in larval rearing, isotope labeling, and protein expression is shown in the schematic of FIG. 1. In order to maximize growth of young larvae and to save valuable isotope labeling diet, newly hatched insects are raised on a classical agar based (gelatinous) diet including primarily pinto beans and alfalfa meal, as well as vitamins and other nutritional supplements, for the first 7-10 days, until the 3rd instar, at which time they are switched to an isotope-labeled algae containing diet. The major components of the classical *T. ni* diet are alfalfa, pinto beans, wheat germ, and brewer's yeast hydrolysate. In certain embodiments, the isotope-labeled algae diet retains small amounts of each of these components for taste and texture.

Methods of using baculovirus to drive expression of recombinant proteins in *T. ni* larvae are known in the art. Baculovirus infection methods include, for example, infection by injection, oral infection by feeding, and infection using aerosolized baculovirus.

As indicated in FIG. 1, in one embodiment of the disclosed methods, the larvae are infected via injection with a baculovirus vector after reaching the 5th instar. Typically 5 microliters of a titered solution containing approximately $5 \times 10^5$ virus particles is used (Hale et al. 2002 *J. Biochem Biophys Methods* 50(2-3):233-43. The yield of isotope-labeled recombinant protein achieved using infection by injection may be optimized as discussed in Example 5.

In another embodiment, the larvae are infected using an oral route of infection. For example, a baculovirus vector which allows for simultaneous expression of both the wild-type polyhedrin gene and the recombinant protein of interest may be utilized to produce orally infective polyhedral inclusion bodies (PIBs). Expression of the AcMNPV polyhedrin protein, results in the formation of a crystalline matrix that protects the virus in the insect digestive tract (termed an "occluded" virus) (O'Reilly, D. R., 1997 *Methods Mol. Biol.* 62:235-46.) Orally infectious PIBs can be purified from insect cells, e.g., Sf9 cells, infected with the above baculovirus vector. Purified PIBs are subsequently used to orally infect *T. ni*. larvae. For example, by applying drops of purified PIBs (~$10^7$ PIBs per cube) to small cubes of insect diet, mass oral infection of the larvae can be accomplished. The yield of isotope-labeled recombinant protein achieved using oral infection may be optimized as discussed in Example 6.

Figure 3:
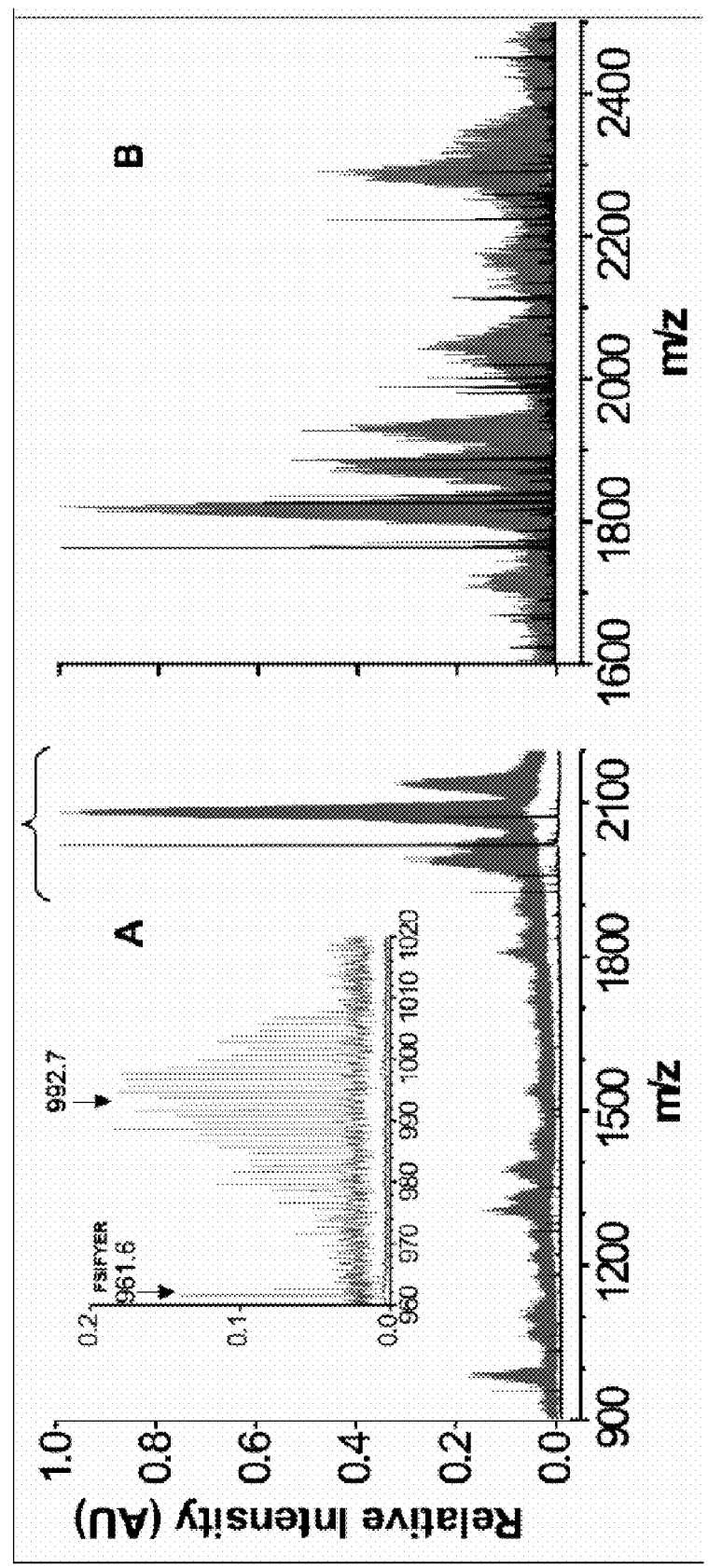
FIG. 3 shows panels from the mass spectra of trypsinized 75 (Panel A) and 150 kDa (Panel B) proteins isolated from larvae raised on $^{13}$C diet.
Figure 4:
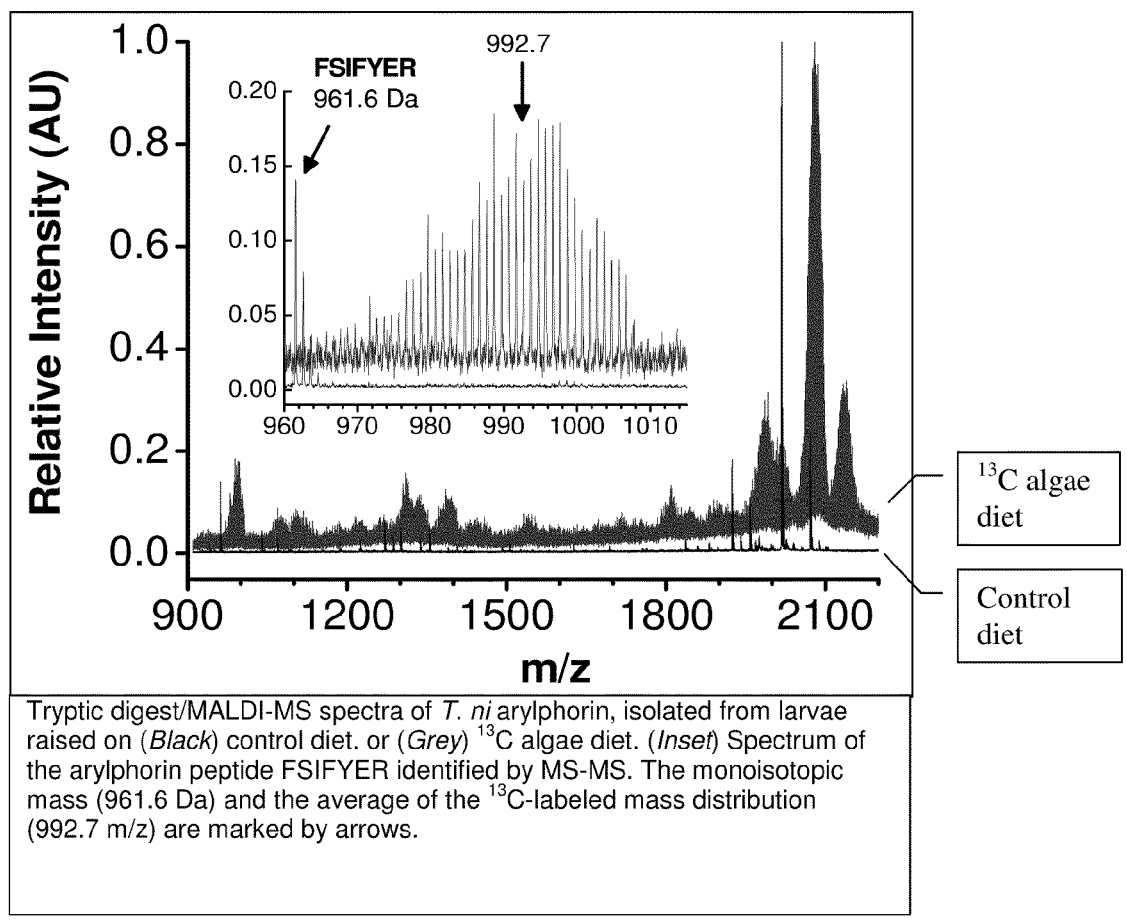
FIG. 4 shows an expanded view of Panel A from FIG. 3. Tryptic digest/MALDI-MS spectra of *T. ni* arylphorin, isolated from larvae raised on (Black) control diet. or (Grey) $^{13}$C algae diet. (Inset) Spectrum of the arylphorin peptide FSI-FYER identified by MS-MS. The monoisotopic mass (961.6 Da) and the average of the $^{13}$C-labeled mass distribution (992.7 m/z) are marked by arrows.
Figure 5:
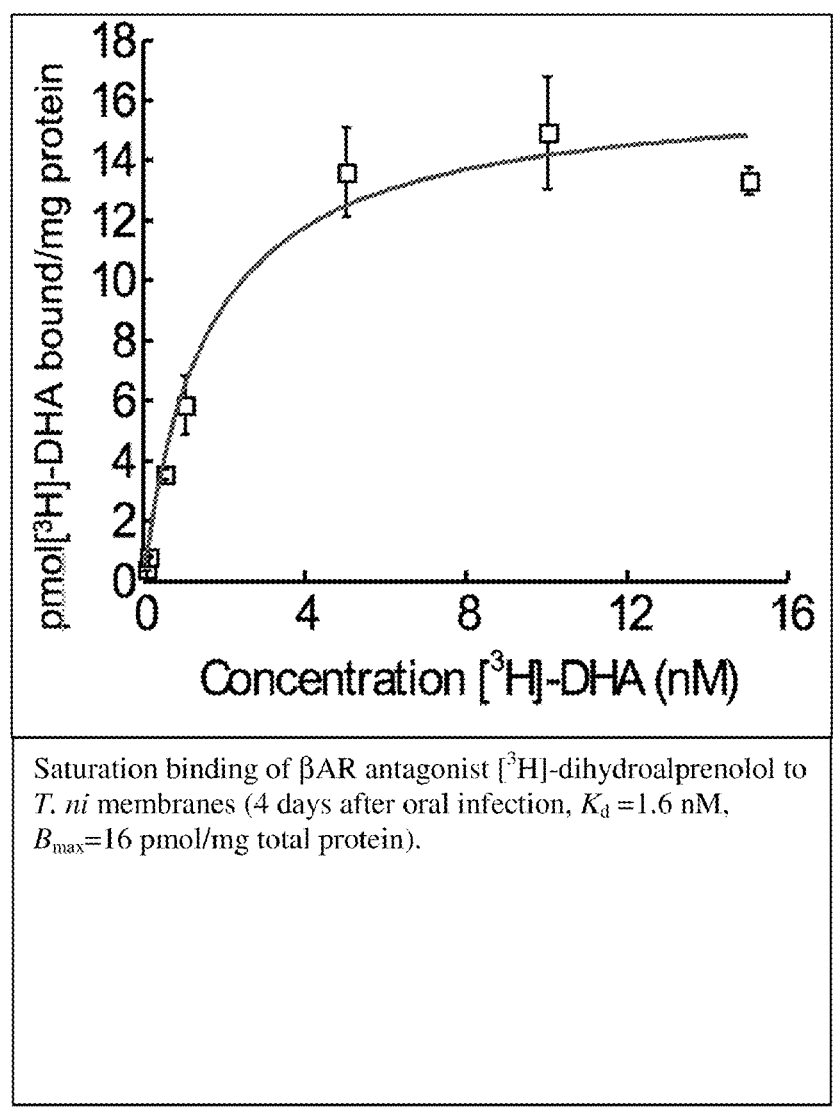
FIG. 5 shows the saturation binding of βAR antagonist [$^3$H]-dihydroalprenolol to *T. ni* membranes (4 days after oral infection, $K_d$=1.6 nM, $B_{max}$=16 pmol/mg total protein).

In another embodiment, the larvae are infected using aerosolized baculovirus as described in U.S. Pat. No. 7,261,886, issued Aug. 28, 2007. FIGS. 3-5 and Columns 3-5 of U.S. Pat. No. 7,261,886 describing methods of infection using aerosolized baculovirus are incorporated by reference herein.

In some embodiments, expression of a recombinant protein of interest in a *T. ni* larva is accomplished using a non-baculovirus based expression method. For example, a nucleic acid sequence which encodes a recombinant protein may be stably integrated into the genome of the larva thereby producing a transgenic larva. Methods of producing transgenic larva are known in the art. See, for example, Markaki M. et al. (2007) *Transgenic Res.* 16(1): 99-107, wherein the germ-line transformation and expression of a cDNA encoding human growth hormone in transgenic *Drosophila* using the Minos transposon is reported, and U.S. Pat. No. 6,130,074, issued Oct. 10, 2000, wherein the production of *T. ni* transgenic for the p74 viral gene is described.

Isolation of a Recombinant Stable-Isotope Labeled Protein from a Baculovirus Infected *T. ni* Larvae

*T. ni* larvae provide a suitable starting material for isolation, in part, because of the high levels of recombinant protein expression that can be achieved per larva. As indicated in Example 3, a single larva is capable of expressing approximately 24 µg of recombinant β2AR protein. High level expression is particularly important where the isolated recombinant protein will be utilized in NMR studies since these experiments require large amounts (e.g., milligrams) of high-quality purified protein.

Stable isotope-labeled recombinant proteins can be isolated from *T. ni* larvae according to a variety of suitable methods. Generally, these methods include the following steps: harvest and optional freezing of the larvae, optional dissection and removal of the gut tube, homogenization and solubilization of the larval material, and purification of the recombinant protein.

Exemplary methods for isolating recombinant proteins from *T. ni* membrane vesicles are provided by Hale et al. 2001 *J. Biochem. Biophys. Methods* 50: 233-243, in sections 2.3 and 2.5, which sections are incorporated herein by reference.

*T. ni* larvae contain a large amount of protease activity. As such, in certain aspects of the disclosed methods it is desirable to limit proteolysis which may occur prior to purification. By removing the gut tube of *T. ni* larvae prior to solubilization of the larvae, exposure of the isotope-labeled recombinant protein to digestive proteases contained therein is limited. In an exemplary embodiment, larvae may be anesthetized on ice and placed in a dissecting dish containing phosphate buffered saline and protease inhibitors. A longitudinal incision is made along the back of the insect. The gut tube is then teased out and can be removed without rupture.

Dissection greatly reduces proteolysis, but the gut is not the only source of protease activity in an insect larva. Lysed cells in the remaining carcass also release proteases. It may therefore be desirable to protect the recombinant protein from proteolysis during homogenization/lysis, solubilization, and up until purification, which eliminates the vast majority of proteases from the sample. For example, *T. ni* carcasses may be solubilized in the presence of a protease inhibitor cocktail. One protease inhibitor cocktail suitable for use in the disclosed methods comprises benzamidine, leupeptin, phenylmethylsulfonyl fluoride, and Roche Complete™ tablets). Additional protease inhibitor cocktails suitable for use with the disclosed methods are known in the art. See for example, Hale et al. 2002 *J. Biochem. Biophys. Methods* 50: 233-243, wherein a combination of aprotinin, leupeptin, pepstatin A, and phenylmethylsulfonyl fluoride is utilized.

Once a protein containing fraction has been isolated according to the methods described above, the recombinant protein of interest, can be isolated and purified using a variety of protein isolation and purification methods known in the art. Of particular interest, are methods which make use of specific affinity tags present on the recombinant protein of interest. Suitable affinity tags include, for example, N-terminal FLAG and C-terminal 6His. Thus, in one aspect of the disclosed methods, the isotope-labeled recombinant protein comprises an affinity tag, e.g., an N-terminal FLAG tag, a C-terminal 6His tag or both. Where the isotope-labeled recombinant protein comprises an N-terminal FLAG tag, an antibody affinity column that binds the N-terminal FLAG epitope (e.g., anti-FLAG M1) may be used to purify the protein. Similarly, where the isotope-labeled recombinant protein comprises a C-terminal 6His tag, a nickel charged Chelating Sepharose Fast Flow (GE Healthcare (Ni column) may be used. Where the isotope-labeled recombinant protein comprises both an N-terminal FLAG tag and a C-terminal 6His tag, the protein may be purified in successive steps using the appropriate columns. Many additional affinity tags are known in the art and those of skill in the art can readily modify the type and location of the affinity tag used. For example, in one embodiment, a C-terminal FLAG tag and/or an N-terminal 6His tag may be used.

For receptor proteins, a ligand affinity column may also be used. For example, in the case of the $\beta_2AR$, an alprenolol ($\beta_2AR$ antagonist) affinity column can be used to selectively isolate $\beta_2AR$ protein that retains ligand-binding activity. Further concentration of proteins purified according to the above methods can be achieved using appropriately sized filters, e.g., a 100 kDa Amicon filter in the case of $\beta_2$AR.

Recombinant Proteins of Interest

The methods disclosed herein may be applied to the labeling and isolation of any recombinant protein which can be expressed in a T. ni larvae and for which a stable isotope-labeled version of the protein is desired. In one aspect, the disclosed methods find use in the isolation and preparation of recombinant proteins for use in NMR analysis. Of particular interest, are mammalian membrane proteins, e.g., G-Protein Coupled Receptors (GPCR)s.

Any known GPCR is suitable for use in connection with the disclosed methods. A disclosure of the sequences and phylogenetic relationships between 277 GPCRs is provided in Joost, P. and Methner, A. 2002 *Genome Biol.* 3(11):research0063.1-0063.16. Table 1 of this reference, which provides an example list of names, accession numbers, and abbreviations for GPCRs, is incorporated by reference herein.

The methods may be used, by way of exemplification, for purinergic receptors, vitamin receptors, lipid receptors, peptide hormone receptors, non-hormone peptide receptors, non-peptide hormone receptors, polypeptide receptors, protease receptors, receptors for sensory signal mediator, and biogenic amine receptors.

It is recognized that both native (naturally occurring) and altered native (non-naturally occurring) GPCRs may be used in the disclosed methods. In certain embodiments, therefore, an altered native GPCR is utilized (e.g. a native GPCR that is altered by an amino acid substitution, deletion and/or insertion) such that it binds the same ligand as a corresponding native GPCR.

As such, the following GPCRs (native or altered) find particular use in the subject methods: cholinergic receptor, muscarinic 3; melanin-concentrating hormone receptor 2; cholinergic receptor, muscarinic 4; niacin receptor; histamine 4 receptor; ghrelin receptor; CXCR3 chemokine receptor; motilin receptor; 5-hydroxytryptamine (serotonin) receptor 2A; 5-hydroxytryptamine (serotonin) receptor 2B; 5-hydroxytryptamine (serotonin) receptor 2C; dopamine receptor D3; dopamine receptor D4; dopamine receptor D1; histamine receptor H2; histamine receptor H3; galanin receptor 1; neuropeptide Y receptor Y1; angiotensin II receptor 1; neurotensin receptor 1; melanocortin 4 receptor; glucagon-like peptide 1 receptor; adenosine A1 receptor; cannabinoid receptor 1; and melanin-concentrating hormone receptor 1.

Of particular interest in one embodiment of the disclosed methods is the β2 adrenergic receptor (β2AR).

Additional proteins of interest include membrane channel proteins and transporters.

Stable Isotope-Labeled Recombinant Proteins

The methods disclosed herein comprise isolating a stable isotope-labeled recombinant protein from a *Trichoplusia ni* larva. Generally, at least 60% of the atoms of a given element in the isolated, stable-isotope labeled recombinant protein are in the desired stable isotopic form, usually at least 65%, 70%, 75%, 80%, 85%, 90%, 95% or 99.9%. For example, in one embodiment at least 65%, at least 70%, at least 75%, at least 80%, at least 85%, at least 90%, at least 95% or at least 99.9% of the carbon atoms in the isotope-labeled recombinant protein are $^{13}$C. In another embodiment, at least 60%, at least 65%, at least 70%, at least 75%, at least 80%, at least 85%, at least 90%, at least 95% or at least 99.9% of the nitrogen atoms in the isotope-labeled recombinant protein are $^{15}$N. In a further embodiment, at least 65%, at least 70%, at least 75%, at least 80%, at least 85%, at least 90%, at least 95%, or at least 99.9% of the carbon atoms in the isotope-labeled recombinant protein are $^{13}$C, and at least 65%, at least 70%, at least 75%, at least 80%, at least 85%, at least 90%, at least 95%, or at least 99.9% of the nitrogen atoms in the isotope-labeled recombinant protein are $^{15}$N.

Methods for determining the percentage of atoms of a particular element that are in a particular stable isotopic form are known in the art. For example, the extent of stable isotope labeling can be determined by comparing the observed mass (by mass spectroscopy) with that expected based on the amino acid sequence of the protein. Exemplary methods for determining the percentage of isotopic labeling of a protein are also provided in Example 1.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Isotope Labeling of *Trichoplusia ni* Proteins Using $^{13}$C Labeled Blue-Green Algae In order to demonstrate the feasibility of creating an economical *Trichoplusia ni* (*T. ni*) diet for $^{13}$C and $^{15}$N isotope labeling of recombinant proteins expressed in baculovirus infected larvae, the incorporation of $^{13}$C into larval hemolymph proteins in larvae fed a phototrophic microorganism-based diet was examined.

*T. ni* larvae were hatched and raised on control (non-isotope labeled) diet through $2^{nd}$ instar. At $3^{rd}$ instar, the larvae (~20 mg) were split and placed on either fresh control diet, or diet containing ~75% protein calories from $^{13}$C-labeled lyophilized blue-green algae (*Agmenellum quadruplicatum*, provided by Cambridge Isotope Laboratories, Inc., 50 Frontage Road, Andover, Mass.). The larvae continued to grow and develop on either diet, although growth rate and survival were lower for the $^{13}$C blue-green algae based diet (60% vs. 100% survival). Larvae raised on control diet reached $5^{th}$ instar approximately three days faster than those raised on $^{13}$C blue-green algae, although the latter ultimately grew to the same size.

At $5^{th}$ instar, Day 2, larvae weighing ~150-200 mg were sacrificed and their hemolymph was collected (O'Reilly et al. (1994) *Baculovirus Expression Vectors: A Laboratory Manual*, Oxford University Press, Oxford. Hemolymph proteins from insects raised on control and $^{13}$C blue-green algae were analyzed by SDS-PAGE and Coomassie staining. FIG. 2 shows the results of the SDS-PAGE analysis of hemolymph (~1 μl) from *T. ni* raised on control diet (Lane A), and $^{13}$C blue-green algae diet (Lane B). Two prominent bands were observed migrating at 75 and 150 kDa.

The 75 and 150 kDa bands were subsequently cut out and analyzed by trypsin digest/Matrix-Assisted Laser Desorption Ionization Mass Spectrometry (MALDI-MS) and Tandem Mass Spectrometry (MS-MS). Panels from the mass spectra of the trypsinized 75 and 150 kDa proteins are shown in FIG. 3 (Panel A) and FIG. 3 (Panel B) respectively, from both control and $^{13}$C-labeled larvae. In FIGS. 3 and 4, proteins isolated from larvae raised on the control diet are indicated in Black, while proteins isolated from larvae raised on $^{13}$C blue-green algae diet are indicated in Grey.

An expanded view of FIG. 3, (Panel A) is shown in FIG. 4. Tryptic peptides from control protein show sharp Poissonian distributions of mass-to-charge (m/z) with the most intense peaks occurring at the monoisotopic molecular weight (M). Less intense peaks present at M+1, M+2, ... M+5 correspond to peptides containing one or more heavy atoms due to natural isotope abundance. By comparison, peptides from $^{13}$C-labeled proteins show Gaussian peak distributions dramatically shifted to higher m/z. For example, each peak in a quartet of peptides from the 75 kDa protein (FIG. 3, Panel A, 1900-2200 m/z, indicated by brace) is shifted by a constant amount (~60 m/z) larger than the monoisotopic molecular weight. This shift in m/z distribution qualitatively demonstrates that 13C-labeled amino acids in the blue-green algae diet are efficiently incorporated into larval proteins.

Using tandem mass spectrometry (MS-MS), the sequence of a single peptide from the 75 kDa protein (FSIFYER, singly protonated chemical formula $C47H_{65}N_{10}O_{12}$, calculated mass=961.5 Da, observed m/z=961.6—marked with an arrow in FIG. 3, panel A inset and FIG. 4 inset) was identified. This information allowed for the confirmation of the identity of the 75 kDa band as arylphorin (an abundant hemolymph storage protein), and calculation of the abundance of $^{13}$C in control and $^{13}$C-labeled samples. Integrated peak areas were used to calculate the weighted average number of $^{13}$Cs present in each sample. An average of 0.6 $^{13}$C atoms per control FSIFYER peptide, and 30.7 $^{13}$C atoms per $^{13}$C-blue-green algae labeled peptide (corresponding most closely to m/z=992.7, marked with an arrow in FIG. 3, panel A inset, and FIG. 4 inset).

Thus, raising $T.\ ni$ from $2^{nd}$ instar on the labeled blue-green algae diet effectively increased the abundance of $^{13}$C in larval proteins from 1% (natural abundance) to 65%. This degree of isotope labeling is near the maximum predicted (67.5%) for larvae that gained 90% of their weight on a diet containing 75% of protein calories from $^{13}$C-labeled blue-green algae.

Example 2

Orally Infectious Baculovirus for B$_2$AR Overexpression $T.\ ni$ can be infected by injecting baculovirus into the body cavity. This approach has been used to express the Na$^+$/Ca$^{2+}$ exchanger (Hale et al. 2002 *Ann. N.Y. Acad. Sci.* 976:100-2; Hale et al. 2002 *J. Biochem. Biophys. Methods* 50(2-3):233-43; Hale et al. 1999 *Protein Expr. Purif.* 15(1):121-6.) It is also possible to infect larvae by the oral route. In nature, $T.\ ni$ is a host for the *Autographa californica* Multiple Nuclear Polyhedrosis Virus (AcMNPV), a baculovirus transmitted by the oral route. Oral infection requires expression of the AcMNPV polyhedrin protein, which forms a crystalline matrix that protects the virus in the insect digestive tract (termed an "occluded" virus) (O'Reilly, D. R., 1997 *Methods Mol. Biol.* 62:235-46.) Unfortunately, polyhedrin is deleted from most commercially available baculovirus vectors to allow expression of the recombinant insert under the strong polyhedrin promoter.

In order to demonstrate the viability of expressing a recombinant protein of interest, e.g., the GPCR $\beta_2$ adrenergic receptor ($\beta_2$AR), using an orally infective baculovirus, a baculovirus transfer vector was engineered which allowed simultaneous expression of both the wild-type polyhedrin gene and the human $\beta_2$AR. This vector was used to produce orally infectious occluded baculovirus as follows. Sf9 cells were infected with above vector and allowed to grow for approximately four days until their nuclei were filled with polyhedral inclusion bodies (PIBs). The cells were pelleted by centrifugation, and lysed by resuspension and douncing in SDS (0.5%). PIBs were pelleted from the lysate by a high-speed spin, washed with sodium chloride (500 mM), and resuspended in distilled water. $T.\ ni$ larvae were infected with occluded baculovirus by applying drops of purified PIBs (~10$^7$ PIBs per cube) to small cubes of insect diet. Newly molted 5$^{th}$ instar larvae (mass ~100 mg) were starved for 6 hours and then permitted to feed on the infected diet. At four days post infection, larvae appeared sluggish and some clearly displayed signs of baculovirus infection (melanizing and wilting). These larvae were frozen in liquid nitrogen and stored at −80° C. Larvae were subsequently lysed and a crude membrane fraction was prepared. Saturation binding was performed with [$^3$H]dihydroalprenolol, a $\beta$AR antagonist.

The results of the saturation binding experiment are shown in FIG. 5. The expression level of functional $\beta_2$AR in $T.\ ni$ (16 pmol/mg) is comparable to that seen in Sf9 insect cells.

Example 3

Quantification of B$_2$AR Overexpression in *Trichoplusia ni*

NMR spectroscopy requires large amounts (e.g., milligrams) of high-quality purified protein. In order to demonstrate that a membrane protein of interest, e.g. a GPCR, can be sufficiently overexpressed in *Trichoplusia ni* larvae to make this system feasible for NMR protein production, expression levels of the GPCR $\beta_2$ adrenergic receptor ($\beta_2$AR) were measured.

Larvae were injected with 5×10$^5$ plaque forming units of baculovirus for expression of $\beta_2$AR (RockII), a protease stabilized version of $\beta_2$AR. At four days post-infection the larvae were harvested, dissected, and solubilized as in Example 4 below.

Figure 6:
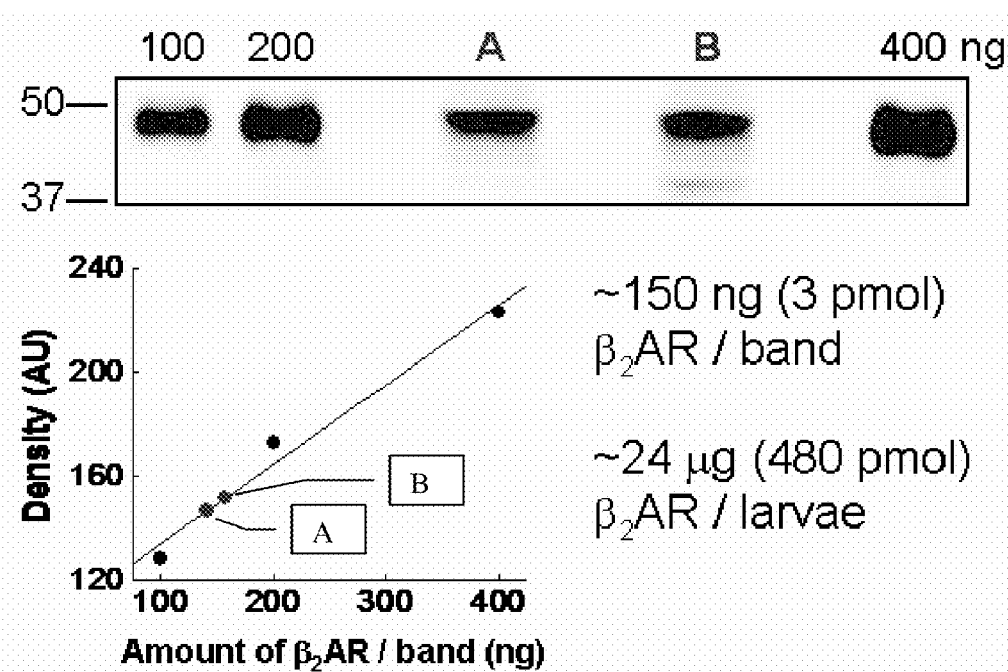
FIG. 6 shows total β$_2$AR expression per larva as estimated by western blot densitometry (anti-FLAG). β$_2$AR purified from Sf9 cells was loaded in known amounts to generate a standard curve. In lanes A and B, $\frac{1}{160}^{th}$ of the total protein from each larva was loaded and quantified.

Samples were analyzed by SDS-PAGE and western blot densitometry using the N-terminal FLAG epitope of the $\beta_2$AR construct (FIG. 6 shows total $\beta_2$AR expression per larvae as estimated by Western blot densitometry (anti-flag)). A standard curve was generated using $\beta_2$AR purified from Sf9 insect cells. Loading 1/160$^{th}$ of the soluble material from individual dissected larva (FIGS. 6, A and B) yielded bands that fell within the linear region of the standard curve (~150 ng/band). Determinations from two different larvae gave similar results: approximately 24 μg (480 pmol) of total $\beta_2$AR per larva. At these expression levels, an NMR experiment needing 5 mg (100 nmol) of receptor could theoretically be performed with material from several hundred larvae, depending on the solubilization and purification efficiency.

Example 4

Purification of B$_2$AR (RockII) from Baculovirus Infected *Trichoplusia ni*

In order to purify $\beta_2$AR from $T.\ ni$ larvae, larvae were injected with baculovirus for expression of $\beta_2$AR (RockII), a protease stabilized version of $\beta_2$AR which retains activity.

Removal of *T. ni* Gut by Dissection to Limit Proteolysis

One major challenge to purification is the large amount of protease activity contained in each larva. The gut tube, which contains digestive proteases, is particularly problematic but can easily be removed by dissection. To harvest, larvae were anesthetized on ice and placed in a dissecting dish containing phosphate buffered saline and protease inhibitors. A longitudinal incision was made along the back of the insect. The gut tube was then teased out and removed without rupture. The remaining carcass consists mostly of fat body (a metabolically active tissue and major site of membrane protein overexpression, O'Reilly et al. *Baculovirus Expression Vectors: A Laboratory Manual.* 1994, Oxford: Oxford University Press. 347) along with various epithelial components and exoskeleton.

Figure 7:
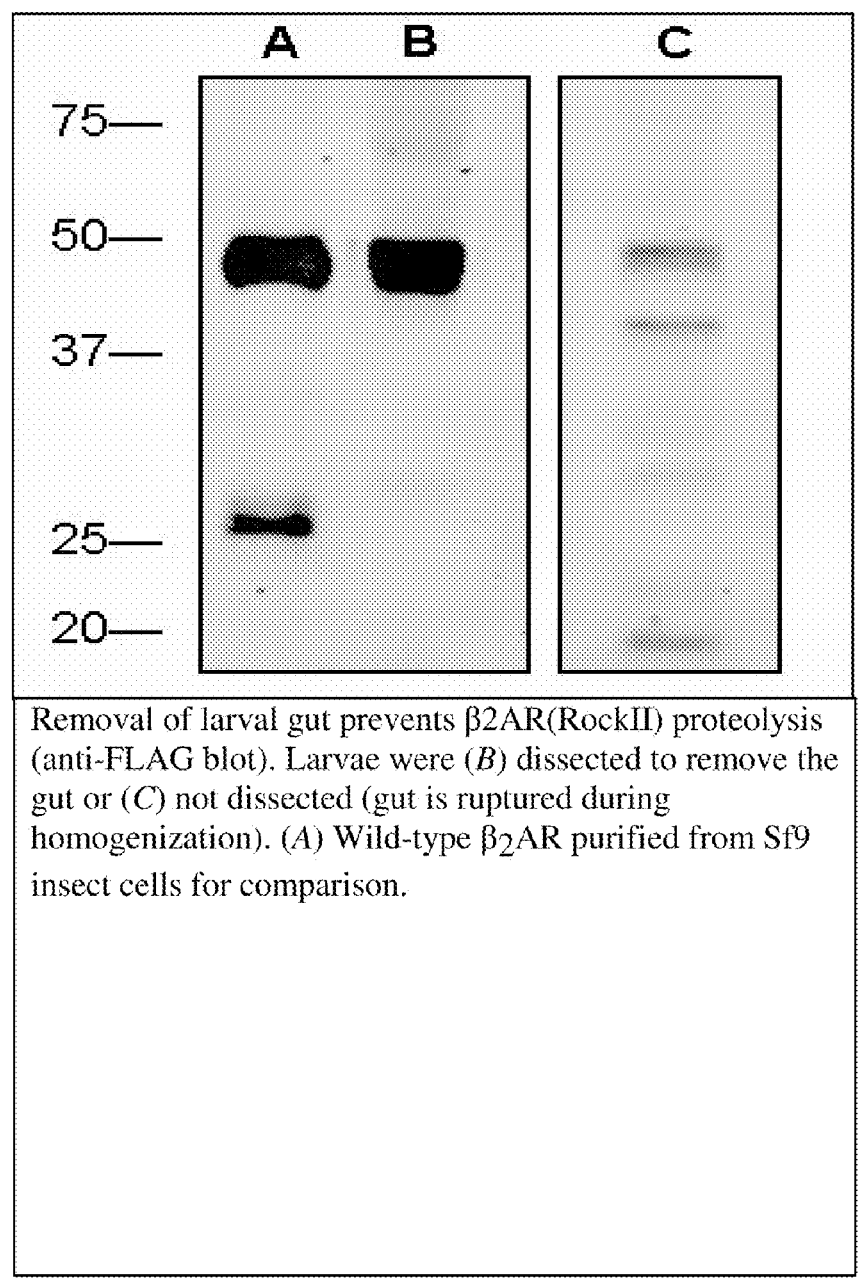
FIG. 7 shows the results of a Western Blot comparing proteolysis of β$_2$AR (RockII) with (Lane B) or without (Lane C) larval gut removal. Lane (A) shows wild-type β$_2$AR purified from Sf9 insect cells for comparison. Larvae were (B) dissected to remove the gut or (C) not dissected (gut is ruptured during homogenization).

To determine whether dissection was effective at reducing proteolysis, $\beta_2AR$ (RockII) solubilized from dissected and non-dissected carcasses was compared. The results of this comparison are provided in FIG. 7. Larvae were homogenized directly in Laemmli sample buffer (10% SDS) and boiled immediately to denature any SDS-resistant proteases. Western blotting demonstrates that dissected carcasses contain nearly 100% intact $\beta_2AR$ (RockII) (FIG. 7, Lane B, 50 kDa band) and demonstrates that the receptor is not proteolyzed in situ by larval proteases). By comparison, significant proteolysis occurs rapidly in non-dissected carcasses when the gut is ruptured (FIG. 7, Lane C), even in the presence of denaturing concentrations of SDS. FIG. 7, Lane A, shows Wild-type $\beta_2AR$ purified from Sf9 insect cells for comparison.

Stabilization of B$_2$AR (RockII) in Detergent after *T. ni* Solubilization Using Protease Inhibitors Dissection greatly reduces proteolysis, but the gut is not the only source of protease activity in an insect larva. Lysed cells in the remaining carcass also release proteases. It may therefore be desirable to protect the receptor from proteolysis during lysis, solubilization, and up until the first affinity chromatography step (anti-FLAG affinity column), which eliminates the vast majority of proteases from the sample.

Figure 8:
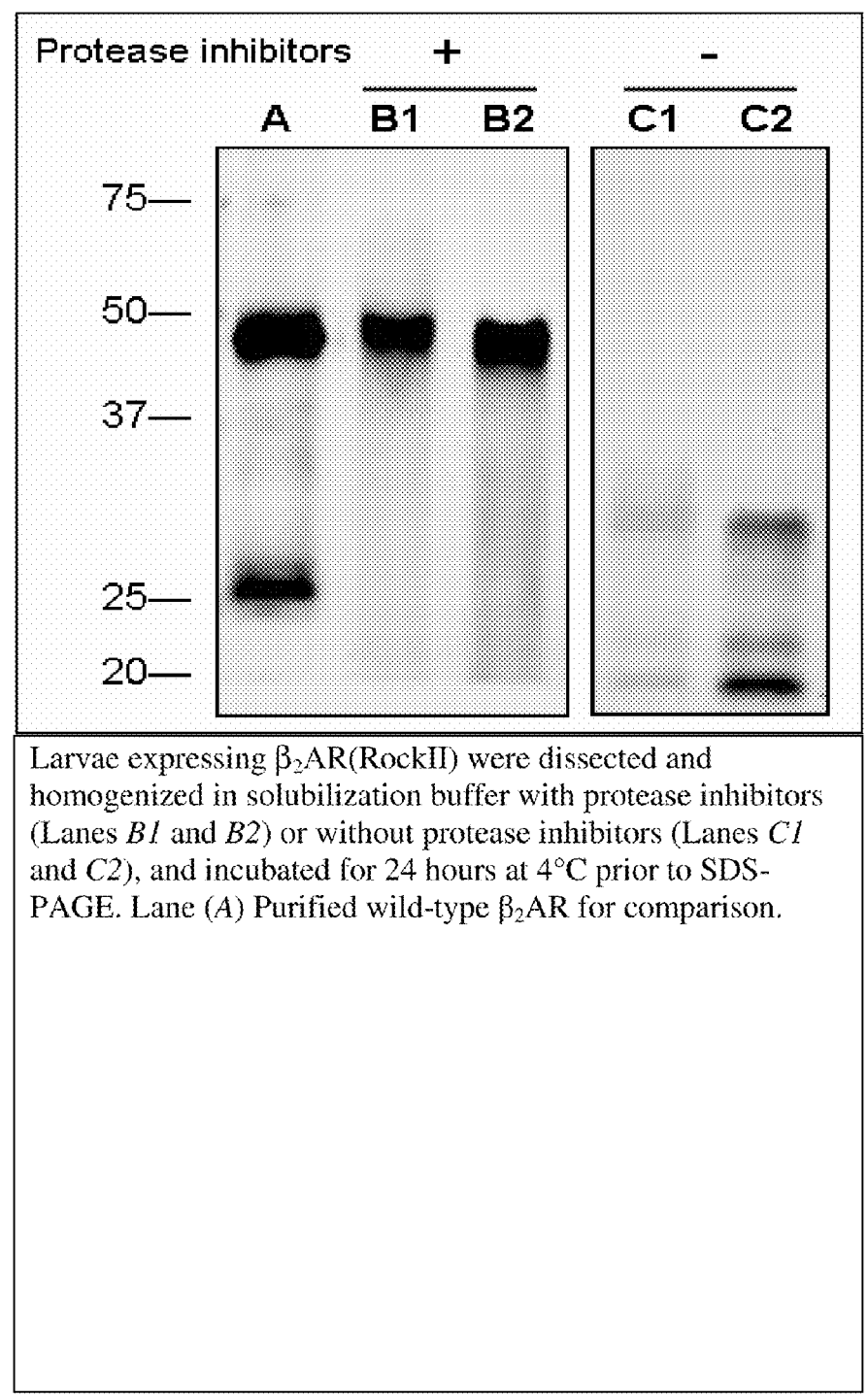
FIG. 8 shows the results of a Western Blot comparing proteolysis of β$_2$AR (RockII) from larvae dissected and homogenized in solubilization buffer with protease inhibitors (Lanes B1 and B2) or without protease inhibitors (Lanes C1 and C2), and incubated for 24 hours at 4° C. prior to SDS-PAGE. Lane (A) shows purified wild-type β$_2$AR for comparison.

To determine conditions for protease inhibition *Ti. ni* larvae expressing $\beta_2AR$ (RockII) were dissected and homogenized in solubilization buffer containing 1% dodecylmaltoside, and 1 µM alprenolol (a high-affinity antagonist that helps stabilize the receptor). Dissected larvae were homogenized is solubilization buffer with protease inhibitors, FIG. 8 (Lanes B1 and B2), or without protease inhibitors, FIG. 8 (Lanes C1 and C2), and incubated for 24 hours at 4° C. prior to SDS-PAGE. In the absence of protease inhibitors, $\beta_2AR$ (RockII) was rapidly proteolyzed upon solubilization (FIG. 8, Lanes C1 and C2). In the presence of a protease inhibitor cocktail (benzamidine, leupeptin, phenylmethylsulfonyl fluoride, and Roche Complete™ tablets) the receptor was protected from proteolysis for >24 hours (FIG. 8, Lanes B1 and B2), providing ample time for anti-FLAG affinity purification of the $\beta_2AR$.

FLAG Purification of $\beta_2AR$ (RockII) from *T. ni*.

Using the conditions determined above to prevent proteolysis, $\beta_2AR$ (RockII) was purified on a small scale from *T. ni* larvae. Three infected larvae were dissected to remove their guts and solubilized in dodecylmaltoside plus protease inhibitors. The soluble material was then pooled and subjected to FLAG affinity chromatography. Various steps in the purification were sampled and analyzed by SDS-PAGE, western blot (anti-FLAG) and Coomassie blue staining. The results of this analysis are provided in FIG. 9.

FIG. 9, Panel (A), shows a Western blot (anti-FLAG) and Panel (B) shows Coomassie blue analysis of the purification. (Lane 1) represents soluble material from dissected larvae, (Lane 2) represents soluble material after passing through an anti-FLAG affinity column, (Lane 3) represents the last column wash prior to elution, (Lane 4) represents the peak fraction eluted from the column containing intact $\beta_2AR$ (RockII), and (Lane 5) represents purified wild-type $\beta_2AR$ for comparison. Lanes (4a and 4b) of Panel B show Coomassie gel Lane 4 scanned with increased sensitivity and resolution.

The peak fraction eluting from the FLAG column (Lane 4) contained intact $\beta_2AR$ (RockII) that was easily detectable as a single 50 kDa band by western blot (FIG. 8, Panel A, note that the $\beta_2AR$ (RockII) molecular weight is slightly different from wild-type $\beta_2AR$). Intact $\beta_2AR$ (RockII) was also detectable by Coomassie staining when the scanner sensitivity and resolution were increased (Panel B, Lanes 4a and 4b, scanned with Odyssey System, Li-Cor Biosciences). This demonstrates that $\beta_2AR$ can be successfully purified from *T. ni* larvae.

Example 5

Infection by Injection Using Recombinant Baculovirus

Injections are performed on early 5$^{th}$ instar larvae as indicated in FIG. 1. Typically 5 microliters of a titered solution containing 5×10$^5$ virus particles is used (Hale et al. 2002 *J. Biochem Biophys Methods* 50(2-3):233-43. After a period of time, larvae are dissected, harvested, and frozen in liquid nitrogen. As indicated in Example 3, $\beta_2AR$ expression was quantified after four days of infection by western blot densitometry (~24 µg/larvae, FIG. 6).

To optimize infection by injection, expression can be quantified in a time course ranging from 1 to 5 days of infection, to ascertain the optimal time of harvest. Functional expression can be quantified by saturation binding with [$^3$H]-dihydroalprenolol. Other parameters that can be investigated include varying the temperature at which the larvae are reared, using different promoters in the baculovirus expression vector, and including an antagonist (alprenolol) in the diet.

By way of example, promoters of interest include the p10 promoter, basic protein promoter, and the polyhedron promoter.

Example 6

Infection by Feeding Occluded Recombinant Baculovirus

To optimize dose and time of oral infection a range of viral doses (~10$^6$ to 10$^8$ occluded viral particles per food cube) as well as duration of infection (1 to 5 days) can be compared. Larvae can be dissected and frozen in liquid nitrogen pending analysis of expression. Intact $\beta_2AR$ can be assessed by western blot densitometry and functionality can be quantified by [$^3$H]-dihydroalprenolol binding. The effect of rearing temperature and the addition of a $\beta_2AR$ antagonist to the diet can also be tested.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present inven-

What is claimed is:

1. A method for isolating a stable isotope-labeled recombinant protein, the method comprising:
isolating a stable isotope-labeled recombinant protein from a *Trichoplusia ni* larva expressing a recombinant protein, which *Trichoplusia ni* larva has ingested a food source comprising stable isotope-labeled algae, thereby resulting in incorporation of a stable isotope into the recombinant protein to produce the stable isotope-labeled recombinant protein.

2. The method of claim 1, wherein the stable isotope is selected from the group consisting of $^{13}$C, $^{15}$N, $^{2}$H, and combinations thereof.

3. The method of claim 1, wherein the stable isotope-labeled algae are produced by growing algae in the presence of at least one of $^{15}$NH$_3$, $^{15}$NO$_3^-$, $^{15}$NO$_2^-$, H$^{13}$CO$_3^-$, $^{15}$N$_2$, $^{13}$CO$_2$, Na$^{15}$NO$_3$ and $^{2}$H$_2$O.

4. The method of claim 1, wherein the *Trichoplusia ni* larva is infected with a baculovirus comprising a nucleic acid encoding said recombinant protein.

5. The method of claim 1 wherein the stable isotope-labeled algae are labeled with $^{13}$C.

6. The method of claim 5, wherein at least 90% of carbon atoms in the stable isotope-labeled algae are $^{13}$C.

7. The method of claim 5, wherein at least 60% of carbon atoms in the stable isotope-labeled recombinant protein are $^{13}$C.

8. The method of claim 1 wherein the stable isotope-labeled algae are labeled with $^{15}$N.

9. The method of claim 8, wherein at least 90% of nitrogen atoms in the stable isotope-labeled algae are $^{15}$N.

10. The method of claim 8, wherein at least 60% of nitrogen atoms in the stable isotope-labeled recombinant protein are $^{15}$N.

11. The method of claim 1, wherein the stable isotope-labeled algae are labeled with both $^{13}$C and $^{15}$N.

12. The method of claim 11, wherein at least 90% of carbon atoms in the stable isotope-labeled algae are $^{13}$C and at least 90% of nitrogen atoms in the stable isotope-labeled algae are $^{15}$N.

13. The method of claim 11, wherein at least 60% of carbon atoms in the stable isotope-labeled recombinant protein are $^{13}$C and at least 60% of nitrogen atoms in the stable isotope-labeled recombinant protein are $^{15}$N.

* * * * *

UNITED STATES PATENT AND TRADEMARK OFFICE
CERTIFICATE OF CORRECTION

| | | Page 1 of 1 |
|---|---|---|
| PATENT NO. | : 8,076,103 B2 | |
| APPLICATION NO. | : 12/338816 | |
| DATED | : December 13, 2011 | |
| INVENTOR(S) | : Kobilka et al. | |

It is certified that error appears in the above-identified patent and that said Letters Patent is hereby corrected as shown below:

In the Specification Under Column 1:

• Please replace Column 1, line no. 13-18 with:

-- FEDERALLY-SPONSORED RESEARCH OR DEVELOPMENT
This invention was made with Government support under contract NS028471 awarded by the National Institutes of Health. The Government has certain rights in this invention. --

Signed and Sealed this
Twenty-third Day of April, 2013

Teresa Stanek Rea
*Acting Director of the United States Patent and Trademark Office*